United States Patent
Banet et al.

(10) Patent No.: US 8,574,161 B2
(45) Date of Patent: *Nov. 5, 2013

(54) VITAL SIGN MONITOR FOR CUFFLESSLY MEASURING BLOOD PRESSURE USING A PULSE TRANSIT TIME CORRECTED FOR VASCULAR INDEX

(75) Inventors: Matthew J. Banet, Del Mar, CA (US); Zhou Zhou, San Diego, CA (US); Marshal Singh Dhillon, San Diego, CA (US); Robert J. Kopotic, Jamul, CA (US); Andrew Stanley Terry, San Diego, CA (US); Henk Visser, II, San Diego, CA (US)

(73) Assignee: Sotera Wireless, Inc., San Diego, CA (US)

( * ) Notice: Subject to any disclaimer, the term of this patent is extended or adjusted under 35 U.S.C. 154(b) by 1113 days.

This patent is subject to a terminal disclaimer.

(21) Appl. No.: 12/138,199

(22) Filed: Jun. 12, 2008

(65) Prior Publication Data

US 2009/0018422 A1    Jan. 15, 2009

Related U.S. Application Data

(60) Provisional application No. 60/943,523, filed on Jun. 12, 2007.

(51) Int. Cl.
 *A61B 5/02*    (2006.01)

(52) U.S. Cl.
 USPC ........................................................ 600/493

(58) Field of Classification Search
 USPC ........................................................ 600/493
 See application file for complete search history.

(56) References Cited

U.S. PATENT DOCUMENTS

| | | |
|---|---|---|
| 4,653,498 A | 3/1987 | New, Jr. et al. |
| 5,316,008 A | 5/1994 | Suga et al. |
| 5,649,543 A | 7/1997 | Hosaka et al. |
| 5,857,975 A | 1/1999 | Golub |
| 5,865,755 A | 2/1999 | Golub |
| 6,592,528 B2 | 7/2003 | Amano et al. |
| 7,179,228 B2 | 2/2007 | Banet |
| 2007/0185393 A1 | 8/2007 | Zhou et al. |
| 2008/0082004 A1 | 4/2008 | Banet et al. |
| 2008/0221399 A1 | 9/2008 | Zhou et al. |

OTHER PUBLICATIONS

Takazawa, et al., "Assessment of Vasoactive Agents adn Vascular Aging by the Second Derivative of Photoplethysmogram Waveform," Hypertension: Journal of the American Heart Association, vol. 32, No. 2, Aug. 1998, pp. 365-370, 7 pages.

International Search Report and Written Opinion, International Patent Application No. PCT/US08/66785, mailed Oct. 9, 2008. (8 pages).

*Primary Examiner* — J. E. Angell
(74) *Attorney, Agent, or Firm* — Michael A. Whittaker; Acuity Law Group, P.C.

(57) ABSTRACT

A method and apparatus for measuring a patient's blood pressure featuring the following steps: 1) measuring a time-dependent optical waveform with an optical sensor; 2) measuring a time-dependent electrical signal with an electrical sensor; 3) estimating the patient's arterial properties using the optical waveform; 4) determining a pulse transit time (PTT) from the time-dependent electrical signal and the time-dependent optical waveform; and 5) calculating a blood pressure value using a mathematical model that includes the PTT and the patient's arterial properties.

23 Claims, 11 Drawing Sheets

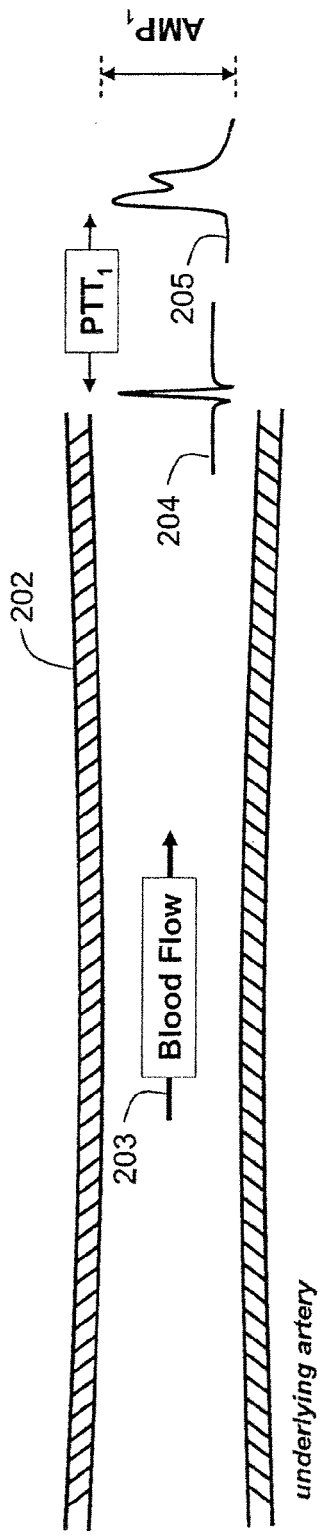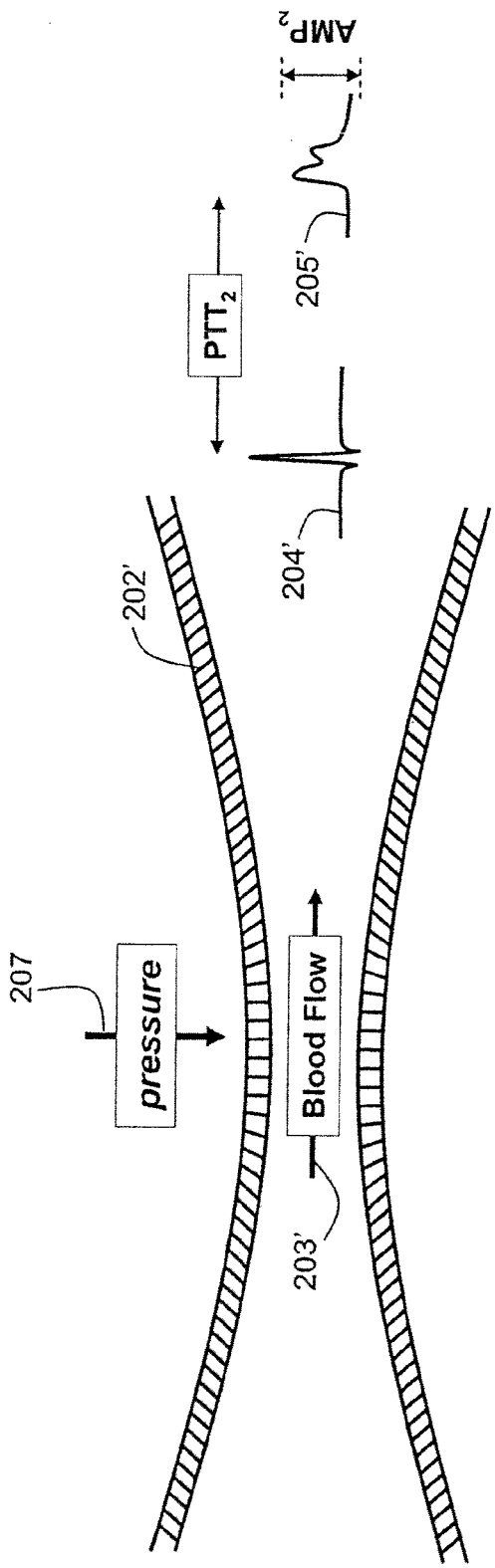
Fig. 8A Pressure-Free Measurement
Fig. 8B Pressure-Dependent Measurement

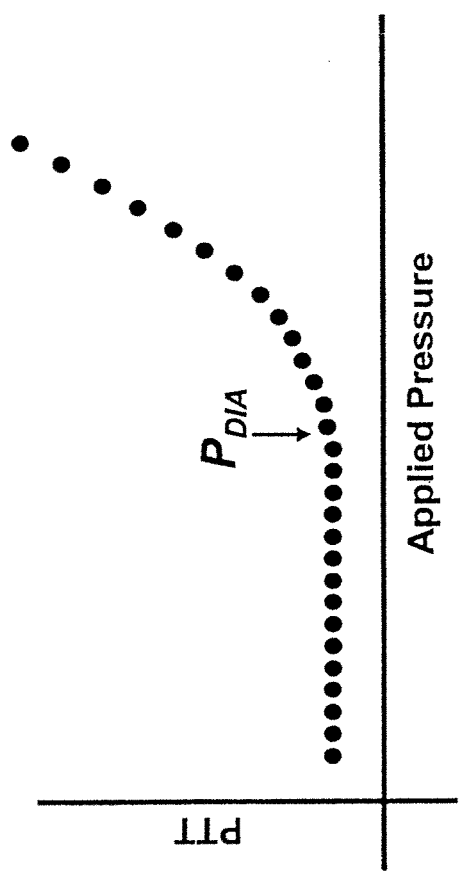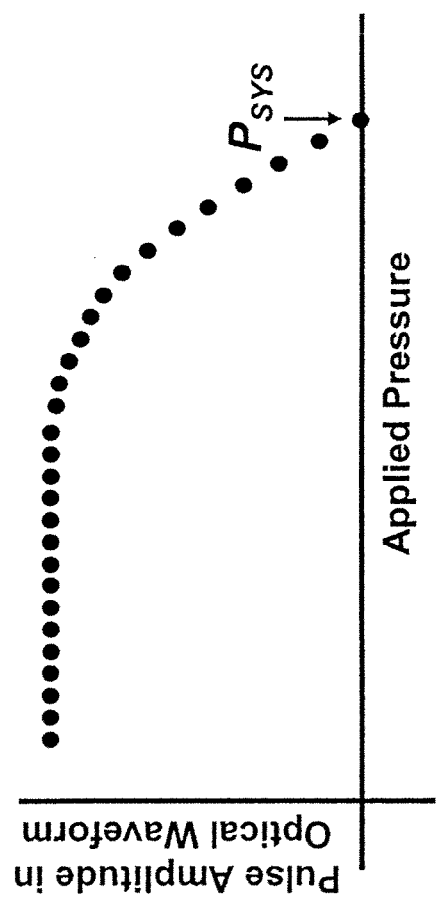

VITAL SIGN MONITOR FOR CUFFLESSLY MEASURING BLOOD PRESSURE USING A PULSE TRANSIT TIME CORRECTED FOR VASCULAR INDEX

CROSS-REFERENCE TO RELATED APPLICATIONS

This application claims the benefit of U.S. Provisional Application No. 60/943,523, filed Jun. 12, 2007, incorporated herein by reference.

FIELD OF THE INVENTION

The present invention generally relates to medical devices for monitoring vital signs, e.g., arterial blood pressure.

BACKGROUND OF THE INVENTION

Pulse transit time (PTT), defined as the transit time for a pressure pulse launched by a heartbeat in a patient's arterial system, has been shown in a number of studies to correlate to both systolic and diastolic blood pressure. In these studies, PTT is typically measured with a conventional vital signs monitor that includes separate modules to determine both an electrocardiogram (ECG) and pulse oximetry. During a PTT measurement, multiple electrodes typically attach to a patient's chest to determine a time-dependent ECG component characterized by a sharp spike called the 'QRS complex'. This feature indicates an initial depolarization of ventricles within the heart and, informally, marks the beginning of the heartbeat and a pressure pulse that follows. Pulse oximetry is typically measured with a bandage or clothespin-shaped sensor that attaches to a patient's finger, and includes optical systems operating in both the red and infrared spectral regions. A photodetector measures radiation emitted from the optical systems and transmitted through the patient's finger. Other body sites, e.g., the ear, forehead, and nose, can also be used in place of the finger. During a measurement, a microprocessor analyses both red and infrared radiation measured by the photodetector to determine the patient's blood oxygen saturation level and a time-dependent waveform called an optical waveform or plethysmograph. Time-dependent features of the optical waveform indicate both pulse rate and a volumetric absorbance change in an underlying artery (e.g., in the finger) caused by the propagating pressure pulse.

Typical PTT measurements determine the time separating a maximum point on the QRS complex (indicating the peak of ventricular depolarization) and a foot of the optical waveform (indicating the beginning the pressure pulse). PTT depends primarily on arterial compliance, the propagation distance of the pressure pulse (closely approximated by the patient's arm length), and blood pressure. To account for patient-dependent properties, such as arterial compliance, PTT-based measurements of blood pressure are typically 'calibrated' using a conventional blood pressure cuff. Typically during the calibration process the blood pressure cuff is applied to the patient, used to make one or more blood pressure measurements, and then removed. Going forward, the calibration blood pressure measurements are used, along with a change in PTT, to estimate the patient's blood pressure and blood pressure variability. PTT typically relates inversely to blood pressure, i.e., a decrease in PTT indicates an increase in blood pressure.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure an ECG and optical waveform, which are then processed to determine PTT.

SUMMARY OF THE INVENTION

Embodiments described herein provide a medical device that makes a cuffless measurement of blood pressure using PTT and a correction that accounts for the patient's arterial properties (e.g., stiffness and size). This correction, referred to herein as a 'vascular index' ('VI'), improves the accuracy of a PTT-based blood pressure measurement by estimating the patient's arterial stiffness by analyzing one or more optical waveforms used in the PTT calculation. A patient's arteries typically stiffen with age, and thus biological age provides an initial estimate arterial stiffness. In certain described embodiments, VI is used along with biological age to further improve the accuracy of PTT-calculated blood pressure, as it serves as a proxy for a 'true' age of the patient's vasculature: patients with elastic arteries for their age will have a VI less than their biological age, while patients with stiff arteries for their age will have a VI greater than their biological age. VI, as used in this application, has the units of years.

As described herein, an optical waveform yields a VI after it is passed through digital filters and processed with a series of mathematical algorithms. The digital filters are implemented using Fast Fourier Transforms ('FFT', also referred to herein as a 'Windowed-Sinc Digital Filter'). Once calculated, the VI is used in combination with the patient's biological age to estimate their arterial properties. These properties are then used to 'correct' the blood pressure determination that was determined by the PTT and thus calculate blood pressure without the need for an external calibration (e.g., without input of an external blood pressure measurement, e.g. an auscultatory or oscillometric measurement).

Embodiments described herein are based on the realization that a PTT-based blood pressure measurement, corrected for the patient's arterial properties using age and VI, shows a better correlation to actual blood pressure than one that is based on PTT alone. Moreover, the correlation between PTT and blood pressure is further improved by measuring PTT using ECG (referred to herein as an 'electrical waveform') and an optical waveform measured near the patient's brachial artery (i.e., near the patient's elbow, superior to the medial epicondyle) or radial artery (e.g., the common site for feeling a pulse near the patient's wrist). Due to the thickness of tissue in these regions, the optical waveform is best measured using a reflective optical sensor. In this configuration, the signal-to-noise ratio of the waveform can be increased by using a multi-sensor array instead of a single sensor, and by choosing an optical wavelength ($\lambda \sim 570$ nm) that works well in reflection-mode geometry for a variety of skin pigmentations. This wavelength may vary slightly (i.e. from 560-580 nm) without affecting the measurement.

The above-described method for calculating blood pressure using PTT and a correction derived from VI can be used in a 'composite' blood pressure measurement technique featuring both pressure-dependent and pressure-free components. Specifically, the composite technique determines blood pressure using: 1) a first, pressure-dependent step that analyzes both PTT and the amplitude of the optical waveform while pressure is applied to the patient's brachial artery; and 2) a second, pressure-free measurement of PTT and information from the pressure-dependent measurement. In routine clinical use, the pressure-free approach typically makes up about 95% of the composite technique's total measurements; pressure-dependent measurements are typically used to calibrate the device and to correct any time-dependent drift in the pressure-free measurements. Drift may occur, for example, due to changes in the patient's temperature, arterial tone and compliance, or cardiac pre-injection period. Both the pressure-dependent and pressure-free measurements use the same measurement system, which features both optical and electrical sensors to measure PTT. The composite technique accurately and continuously determines the patient's blood pressure over an extended time without requiring an external calibration device, e.g., an external blood pressure cuff.

The composite technique is also based on the discovery that PTT, measured in the presence of an applied pressure, typically increases when the applied pressure is equal to or greater than the patient's diastolic blood pressure. As the applied pressure gradually increases to the patient's systolic pressure, PTT continues to increase, typically in a linear manner. When the applied pressure equals systolic blood pressure, the amplitude of an optical waveform measured below the region of applied pressure decreases to zero, and the PTT is no longer measurable. Thus, analyzing both PTT and the optical waveform's amplitude over a suitable range yields the patient's systolic blood pressure. Further analysis of the pressure-dependent increase in PTT yields a calibration that relates PTT and blood pressure for the particular patient. Once determined, these parameters are used with a PTT measured with the same optical and electrical sensors (but no applied pressure) to continuously measure the patient's blood pressure.

PTT, VI and blood pressure, along with other information such as pulse pressure, blood pressure variability, heart rate, heart rate variability, respiratory rate, pulse oximetry, pulse wave velocity, and temperature, are analyzed with a hand-held device that includes many features of a conventional personal digital assistant (PDA). The device includes, for example, a microprocessor that runs an icon-driven graphical user interface (GUI) on a color, liquid crystal display attached to a touch panel. A user selects different measurement modes, such as continuous measurements in the hospital, one-time measurements at home and in the hospital, and 24-hour ambulatory measurements, by tapping a stylus on an appropriate icon within the GUI. The device also includes several other hardware features commonly found in PDAs, such as short-range (e.g., Bluetooth® and WiFi®) and long-range (e.g., CDMA, GSM, IDEN) modems, global positioning system, digital camera, and barcode scanner.

In one aspect, for example, the described embodiment provides a method for measuring a patient's blood pressure that includes: 1) measuring a time-dependent optical waveform with an optical sensor; 2) measuring a time-dependent electrical waveform with an electrical sensor; 3) determining a VI from the time-dependent optical waveform; 4) determining a PTT from the time-dependent electrical signal from the heart and the time-dependent optical waveform; 5) calculating a blood pressure value using a mathematical model that includes PTT and a predetermined relationship between PTT and blood pressure; and 6) correcting the blood pressure with the VI and the patient's biological age.

In embodiments, the method includes determining the VI by analyzing the properties (e.g., taken from the second derivative) of the first optical waveform. To measure the optical waveform, for example, the optical sensor typically operates in a transmission or reflection-mode geometry near the patient's brachial, radial or ulnar arteries. Typically 3 electrodes, disposed on the patient in a conventional 'Einthoven's triangle' configuration, detect electrical signals which, once processed, determine the electrical waveform.

The embodiments of the invention have one or more of the following advantages. In general, the device described herein uses both PTT and VI to make a continuous, cuffless measurement of blood pressure. This allows, for example, patients to be better monitored in hospitals and medical clinics. Moreover, the device combines all the data-analysis features and form factor of a conventional PDA with the monitoring capabilities of a conventional vital sign monitor. This results in an easy-to-use, flexible device that performs one-time, continuous, and ambulatory measurements both in and outside of a hospital. Moreover, the optical and electrical sensors can be connected to a comfortable, lightweight body sensor that wirelessly communicates with monitor. This eliminates the wires that normally tether a patient to a conventional vital sign monitor, thereby increasing patient comfort and enabling mobility.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 8A and 8B show, respectively, schematic drawings of pressure-free and pressure-dependent measurements used in the composite technique.

FIGS. 11A and 11B show graphs of, respectively, PTT and the amplitude of the optical waveform as a function of pressure.

DETAILED DESCRIPTION

Figure 1:
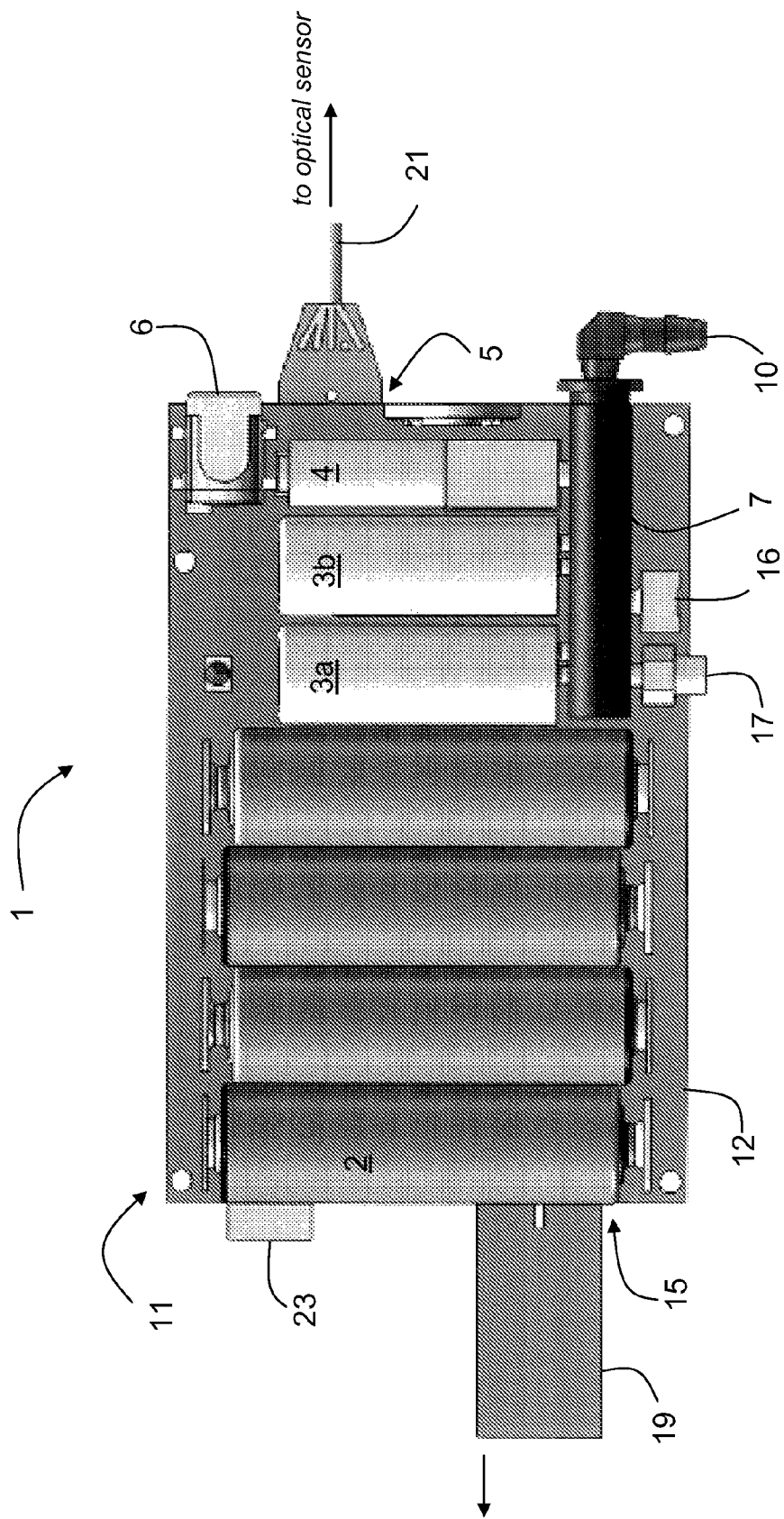
FIG. 1 is a top view of a circuit board used in the body sensor.
Figure 2:
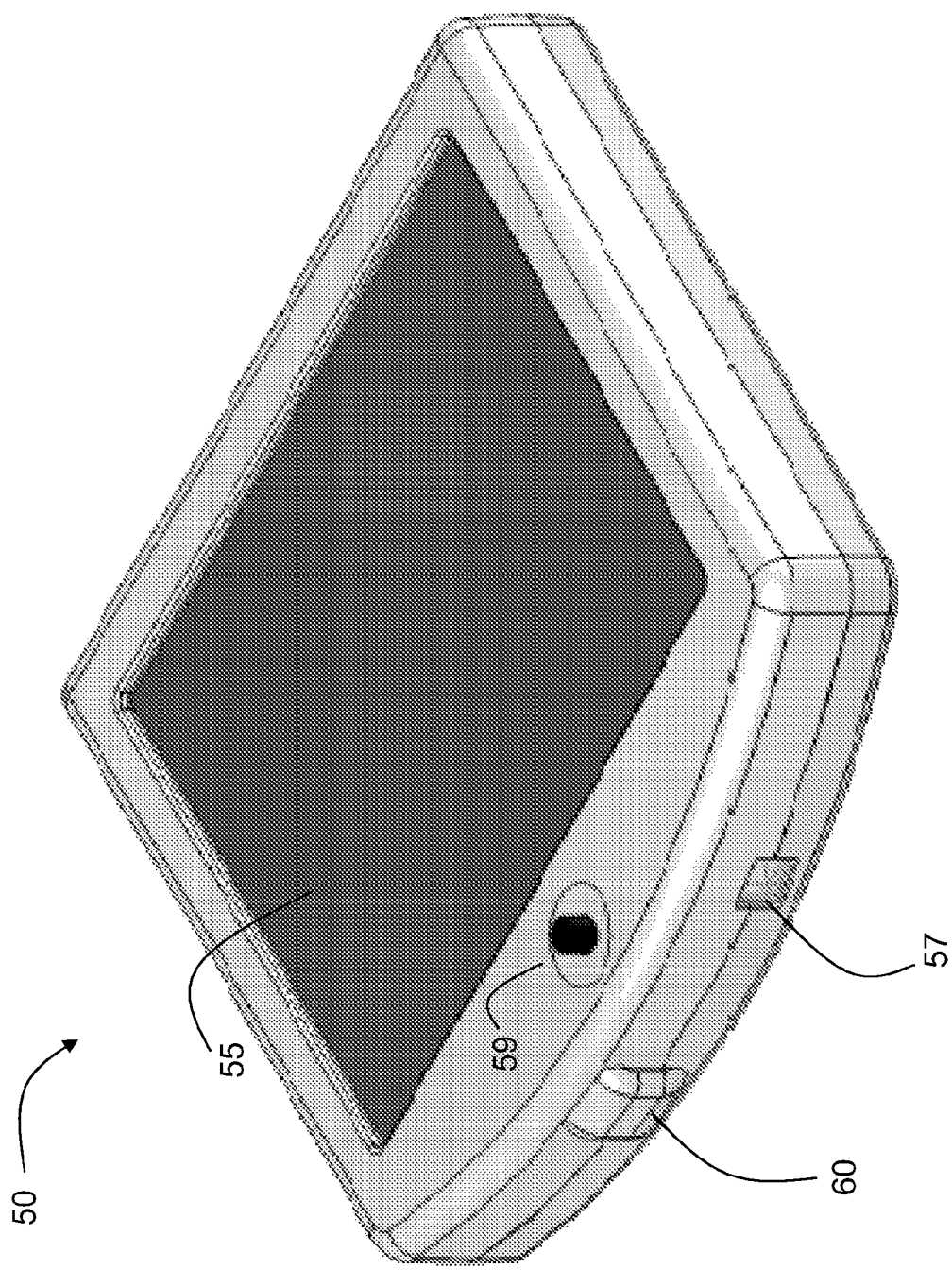
FIG. 2 is a three-dimensional plan view of the monitor.

FIGS. 1 and 2 show a system featuring a body sensor and monitor that performs a PTT-based blood pressure measurement, corrected for VI, on a patient. The blood pressure measurement features pressure-dependent and pressure-free measurements. The system measures: i) an optical waveform from the patient with an optical sensor; ii) an electrical waveform using an electrical sensor featuring multiple ECG electrodes; and iii) a pressure waveform using armband featuring an inflatable bladder. A first algorithm operating on the body sensor, described in detail below, analyzes the optical waveform to estimate VI. A second algorithm calculates PTT from the electrical and optical waveforms, and uses this value to calculate blood pressure. VI and biological age are then compared to a predetermined correction factor and used adjust the PTT-determined blood pressure value.

FIG. 1 shows a top view of the body sensor 1 used to conduct the above-described measurements. The body sensor 1 features a single circuit board 12 including connectors 5, 15 that connect through separate cables 19, 21 to, respectively, the electrical sensor (electrodes worn on the patient's chest) and optical sensor (worn on the patient's wrist). During both pressure-dependent and pressure-free measurements, these sensors measure electrical and optical signals that pass through the connectors 5, 15 to discrete circuit components 11 on the bottom side of the circuit board 12. The discrete components 11 include: i) analog circuitry for amplifying and filtering the time-dependent optical and electrical waveforms; ii) an analog-to-digital converter for converting the time-dependent analog signals into digital waveforms; and iii) a microprocessor for processing the digital waveforms to determine blood pressure according to the composite technique, along with other vital signs.

To measure the pressure waveform during a pressure-dependent measurement, the circuit board 12 additionally includes a small mechanical pump 4 for inflating the bladder within the armband, and first and second solenoid values 3a, 3b for controlling the bladder's inflation and deflation rates. The pump 4 and solenoid valves 3a, 3b connect through a manifold 7 to a connector 10 that attaches through a tube (not shown in the figure) to the bladder in the armband, and additionally to a digital pressure sensor 16 that senses the pressure in the bladder. The first solenoid valve 3a couples through the manifold 7 to a small 'bleeder' valve 17 featuring a small hole that slowly releases pressure. The second solenoid valve 3b is coupled through the manifold 7 and rapidly releases pressure. Typically both solenoid valves 3a, 3b are closed as the pump 4 inflates the bladder. For measurements conducted during inflation, pulsations caused by the patient's heartbeats couple into the bladder as it inflates, and are mapped onto the pressure waveform. The digital pressure sensor 16 generates an analog pressure waveform, which is then digitized with the analog-to-digital converter described above. The microprocessor processes the digitized pressure, optical, and electrical waveforms to determine systolic, mean arterial, and diastolic blood pressures. Once these measurements are complete, the microprocessor immediately opens the second solenoid valve 3b, causing the bladder to rapidly deflate.

Alternatively, for measurements done on deflation, the pump 4 inflates the bladder to a pre-programmed pressure above the patient's systolic pressure. Once this pressure is reached, the microprocessor opens the first solenoid valve 3a, which couples to the 'bleeder' valve 17 to slowly release the pressure. During this deflation period, pulsations caused by the patient's heartbeat are coupled into the bladder and are mapped onto the pressure waveform, which is then measured by the digital pressure sensor 16. Once the microprocessor determines systolic, mean arterial, and diastolic blood pressure, it opens the second solenoid valve 3b to rapidly evacuate the pressure.

Four AA batteries 2 mount directly on the circuit board 12 to power all the above-mentioned circuit components. The board 12 additionally includes a plug 6 which accepts power from a wall-mounted AC adaptor. The AC adaptor is used, for example, when measurements are made over an extended period of time. A rugged plastic housing (not shown in the figure) covers the circuit board 12 and all its components. A Bluetooth transmitter 23 is mounted directly on the circuit board 12 and, following a measurement, wirelessly transmits information to an external monitor.

The optical modules within the optical sensor typically include an LED operating near 570 nm, a photodetector, and an amplifier. This wavelength is selected because, when deployed in a reflection-mode geometry, it is particularly sensitive to volumetric absorbance changes in an underlying artery for a wide variety of skin pigmentations. A preferred sensor is described in the following co-pending patent application, the entire contents of which are incorporated herein by reference: SYSTEM FOR MEASURING VITAL SIGNS USING AN OPTICAL MODULE FEATURING A GREEN LIGHT SOURCE (U.S. Ser. No. 11/307,375; filed Feb. 3, 2006). Typically, multiple optical modules are used in the sensor to increase the probability that an underlying (or proximal) artery is measured, thus increasing the signal-to-noise ratio of the measurement. Operating in concert, the multiple sensors collectively measure an optical waveform that includes photocurrent generated by each optical module. The resultant signal forms the optical waveform, and effectively represents an 'average'signal measured from vasculature (e.g., arteries, arterioles and capillaries) underneath the sensor. The optical sensor can additionally include LEDs operating near 650 nm and 950 nm in order to make a pulse oximetry measurement.

FIG. 2 shows a three-dimensional plan view of the monitor 50 that receives the Bluetooth-transmitted information. The front face of the monitor 50 includes a touchpanel display 55 that renders an icon-driven graphical user interface, and a circular on/off button 59. During an actual measurement, the touchpanel display 55 renders vital sign information from the body sensor. Such a monitor has been described previously in BLOOD PRESSURE MONITOR (U.S. Ser. No. 11/530,076; filed Sep. 8, 2006) and MONITOR FOR MEASURING VITAL SIGNS AND RENDERING VIDEO IMAGES (U.S. Ser. No. 11/682,177; filed Mar. 5, 2007), the contents of which are incorporated herein by reference. The monitor 50 includes an internal Bluetooth transmitter (not shown in the figure) that can include an antenna 60 to increase the strength of the received signal. To pair with a body sensor, such as that shown in FIG. 1, the monitor 50 includes a barcode scanner 57 on its top surface. During operation, a user holds the monitor 50 in one hand, and points the barcode scanner 57 at a printed barcode adhered to the plastic cover surrounding the body sensor. The user then taps an icon on the touchpanel display 55, causing the barcode scanner 57 to scan the barcode. The printed barcode includes information on the body sensor's Bluetooth transceiver that allows it to pair with the monitor's Bluetooth transceiver. The scanning process decodes the barcode and translates its information to a microprocessor within the monitor 50. Once the information is received, software running on the microprocessor analyzes it to complete the pairing. This methodology forces the user to bring the monitor into close proximity to the body sensor, thereby reducing the chance that vital sign information from another body sensor is erroneously received and displayed.

The above-described system determines the patient's blood pressure using PTT as shown schematically in FIGS. 8A and 8B, and then corrects this value for VI using the algorithm described below. Specifically, it is well know that a patient's arteries stiffen with biological age. This property can thus be used to estimate the patient's vascular stiffness. When used with a PTT-based measurement of blood pressure, which depends strongly on vascular stiffness, biological age can increase the accuracy of the blood pressure measurement. The accuracy of the measurement can be further improved with VI, which serves as a proxy for a 'true' age of the patient's vasculature: patients with elastic arteries for their age will have a VI less than their biological age, while patients with stiff arteries for their age will have a VI greater than their biological age. Therefore, the difference between VI and the patient's biological age can be compared to a pre-determined correction factor to improve the accuracy of a PTT-based blood pressure measurement.

Figure 3:
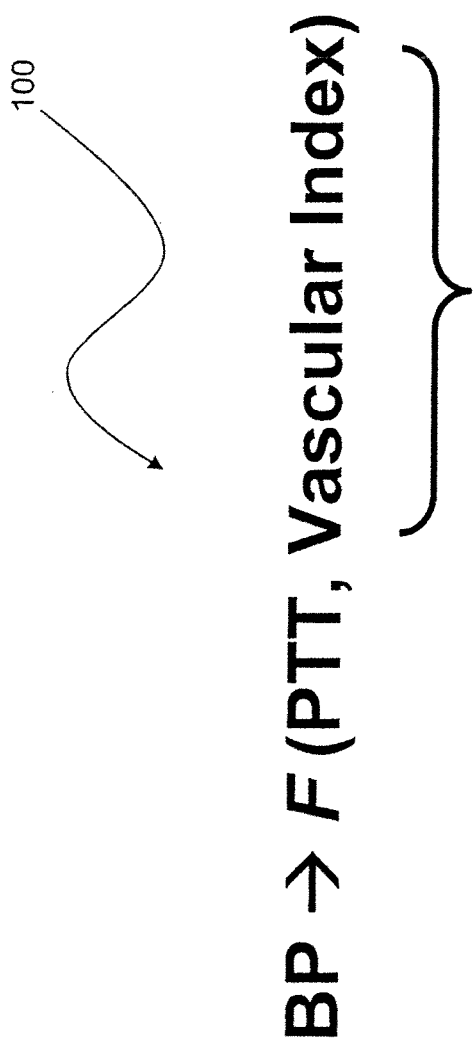
FIG. 3 shows an abstraction of a mathematical equation describing how blood pressure can be calculated from PTT and VI.

FIG. 3, for example, shows an abstraction of a mathematical equation 100 that indicates how blood pressure is calculated from both PTT and VI. As indicated in the figure, VI is preferably calculated using a 6-step algorithm, described in more detail with reference to FIGS. 4A-F, that includes: 1) filtering an optical waveform with an first, fixed-frequency FFT-based filter; 2) taking the first and second derivatives of the filtered waveform; 3) filtering the second derivative with a second, fixed-frequency FFT-based filter; 4) analyzing the waveform using a peak-finding algorithm to determine a patient-specific cutoff frequency; 5) filtering the second derivative with an adaptable-frequency FFT-based filter featuring the patient-specific cutoff frequency; and 6) analyzing the filtered, second derivative to find a series of 'peaks' and 'troughs', the amplitude of which are then processed with a mathematical formula, described below in Equation 1, to calculate VI.

Figure 4:
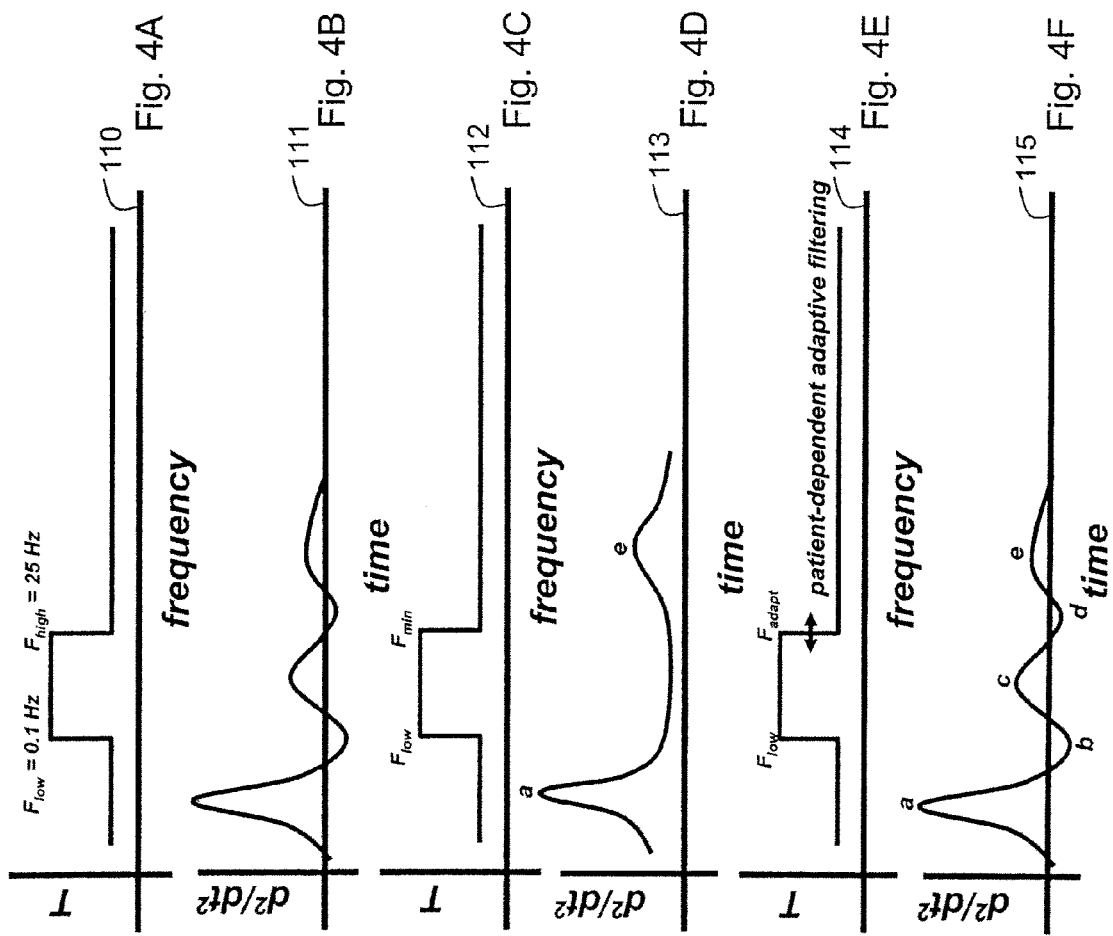
FIGS. 4A, 4C, and 4E are graphs of, respectively, a first fixed-frequency bandpass filter, a second fixed-frequency bandpass filter, and an adaptive bandpass filter used during waveform analysis.
FIG. 4B is a graph of a second derivative of the optical waveform after filtering with the first fixed-frequency bandpass filter of FIG. 4A.
FIG. 4D is a graph of a second derivative of the optical waveform after filtering with the second fixed-frequency bandpass filter of FIG. 4C.
FIG. 4F is a graph of a second derivative of the optical waveform after filtering with the second fixed-frequency and adaptive-frequency bandpass filters of, respectively, FIGS. 4C and 4E.

Referring to FIGS. 4A-F, for the algorithm the optical waveform is first measured and digitized using the analog-to-digital converter within the body sensor. The resultant waveform is then processed using a first, FFT-based digital filter. FIG. 4A, for example, shows a graph 110 of a fixed-frequency filter used to remove extraneous noise from the optical waveform, e.g., noise from external power supplies, fluorescent lights, and patient motion. Typically, the optical waveform is filtered using a filter that passes frequencies between $F_{low}$=0.1 Hz and $F_{high}$=25 Hz, and rejects any frequencies outside of this range. In general, the cutoff frequencies $F_{low}$ and $F_{high}$ are chosen such that the external noise sources are removed, but the fundamental frequencies comprising the optical waveform are unaltered. FFT-based digital filtering algorithms are well known in signal processing, and are described, for example, in: *Numerical Recipes in C*, 1988, Cambridge University Press, the contents of which are incorporated by reference. In one embodiment, the FFT-based filtering algorithm is a digital bandpass filter, implemented as a Finite Impulse Response Windowed-Sinc Filter (FIR-WS filter).

Once filtered, the optical waveform is processed to determine its first and second mathematical derivatives; the latter is shown in the graph 111 of FIG. 4B. The first derivative for each point X is calculated by choosing a window size of N and then taking the difference between the points X+(N/2) and X−(N/2). This difference is typically normalized to the window size N. The second derivative is calculated in the same way, using the first derivative as input. The resulting waveform includes a series of peaks and troughs, described in detail below, that are sensitive to acceleration of a volumetric absorbance change in the artery measured by the optical sensor; the amplitudes of these features are strongly influenced by the artery's vascular properties (e.g., its stiffness).

The first FFT-based filtering process, shown schematically in FIG. 4A, may introduce to the optical waveform a small amount of oscillating noise at the frequency $F_{high}$. This noise can be amplified after taking a second derivative of the waveform, shown in FIG. 4B, and may contribute errors to the VI calculation. To mitigate this, the second derivative is processed with a second digital bandpass filter, shown schematically in the graph 112 of FIG. 4C. $F_{low}$ for the second filter is unchanged from that shown in FIG. 4A, while $F_{min}$ is chosen to be slightly less than $F_{high}$. After filtering, the resulting second derivative lacks any oscillating noise caused by the $F_{high}$ cutoff filter, and typically contains first and second peaks, similar to the peaks 'a' and 'e' shown in the waveform 113 of FIG. 4D. The locations of these peaks are saved in memory, and used as described below to determine various peaks and troughs. Additionally, as shown by the waveform 114 in FIG. 4E, the frequency difference separating peaks 'a' and 'e' yields a new cutoff frequency, $F_{adapt}$, which varies with each patient and is sensitive to their cardiac and vascular properties. $F_{adapt}$ is greater than $F_{min}$, but less than $F_{high}$; it is determined on a patient-specific basis to optimize removal of the oscillating noise in the second derivative, while minimizing removal of features of interest in the waveform.

Once $F_{adapt}$ is determined, the second derivative shown in FIG. 4B is filtered a second time using $F_{low}$ as a low-frequency cutoff and $F_{adapt}$ as a patient-dependent, high-frequency cutoff. FIG. 4F shows a graph 115 of the second derivative waveform following the adaptive filtering process. The waveform has a high signal-to-noise ratio and features a series of peaks and troughs, labeled 'a', 'b', 'c', 'd', and 'e', which are used to calculate VI. In general, these peaks and troughs will be more pronounced, and the VI will be lower, in arteries that have more elasticity. The first peak ('a') and the first trough ('b') are detected using a peak-detecting search window centered on the first peak, as shown in FIG. 4D and described above, used to determine the adaptive filter frequency $F_{adapt}$. The peak-detecting search window is an algorithm that determines the local maximum value of the various peaks. The final peak ('e') is detected using a peak-detecting search window centered on the last peak detected during this step. Finally, the second peak ('c') and second trough ('d') are detected by performing a peak-detecting search window in the interval between the previously detected 'b' trough and the 'e' peak.

Once determined, the amplitude of peaks and troughs 'a' through 'e' can be related to VI using equation 1, below.

$$VI = (A_1 + [(b-c-d-e)/a])/A_2 \qquad 1)$$

where $A_1$ and $A_2$ are predetermined constants. $A_1$ is typically 1.515, and $A_2$ is typically 0.023, as described in the following reference, the contents of which are incorporated herein by reference: *Assessment of Vasoactive Agents and Vascular Aging by the Second Derivative of Photoplethysmogram Waveform*, Takazawa et al., Hypertension 32:365-370, 1998.

Figure 5:
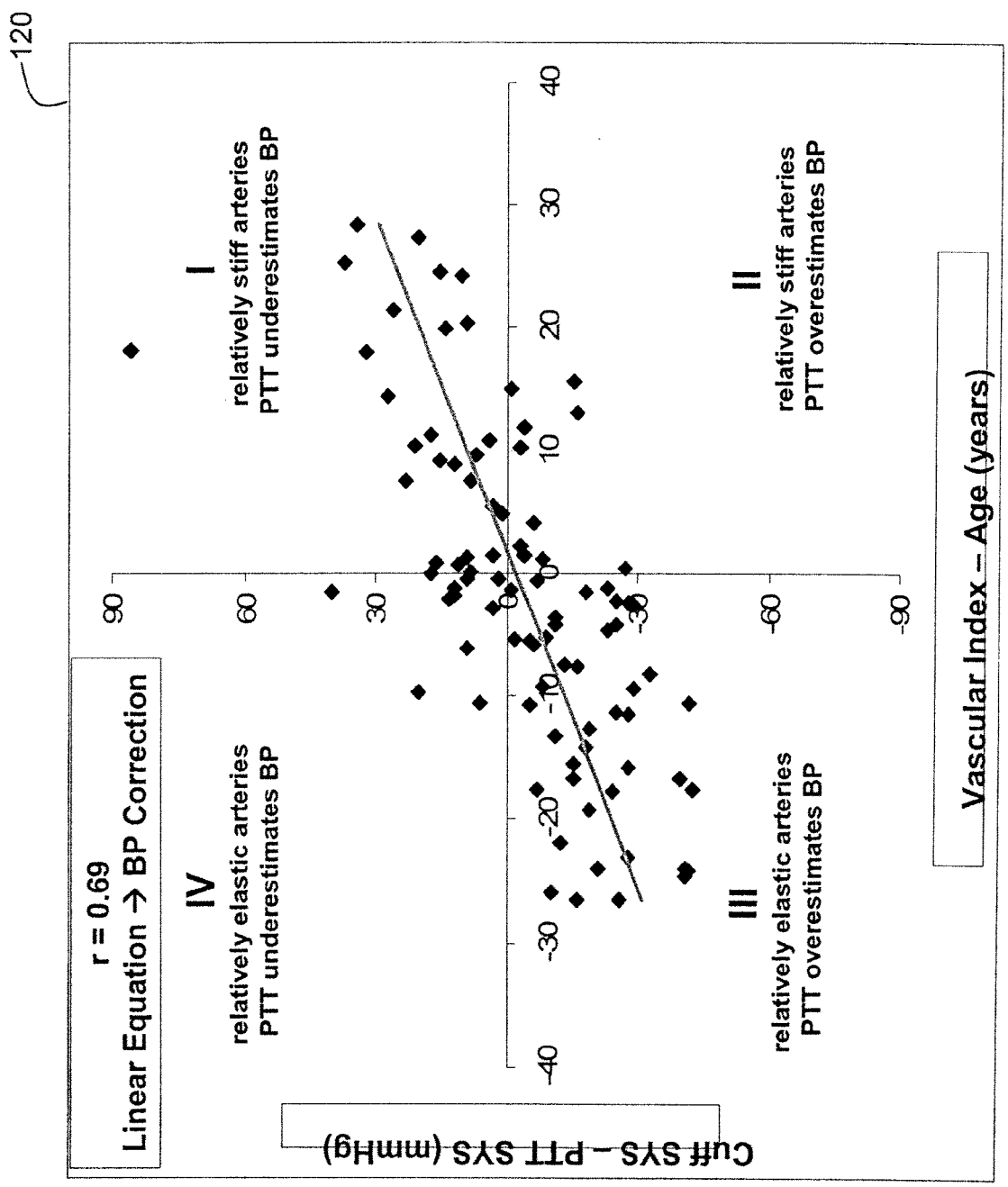
FIG. 5 is a graph of an error in systolic blood pressure vs. the difference between VI and age for a 200-patient study.

Once determined, VI can be used along with the patient's biological age and a predetermined correction factor to improve the accuracy of the PTT-based blood pressure calculation. FIG. 5 illustrates the impact of this correction. It shows a graph 120 of a difference between VI and biological age as a function of the difference between systolic blood pressure measured by a medical professional using a stethoscope with a cuff and aneroid sphygmomanometer ('Cuff SYS' in the figure) and using an uncorrected PTT measurement ('PTT SYS' in the figure). Data for the graph were determined by measuring 200 patients with both a device similar to that shown in FIGS. 1 and 2, and an aneroid sphygmomanometer. The patient's biological age was determined with a survey prior to the measurement. As is clear from the figure, comparison of these parameters yields a systematic, linear relationship, characterized by a correlation coefficient of r=0.69 and shown by the grey line used to fit the data. The slope ($M_{VI}$) and y-intercept ($B_{VI}$) extracted from the fit (1.1 mmHg/years and 2.16 mmHg, respectively) are fixed, predetermined parameters used for the correction. These values, which are determined from a statistically significant number of patients, can be used as the predetermined corrector factor with the above-described algorithm. Specifically, systolic blood pressure can be calculated according to Equation 2, below:

$$SYS\ BP(\text{corrected}) = \text{PTT-Based }SYS\ BP + (VI-\text{Bio Age})*M_{VI}+B_{VI} \qquad 2)$$

Diastolic and mean blood pressures are determined in a similar manner, i.e., by first determining a relationship with PTT, and then correcting for any errors using VI, biological age, and a correction based on a pre-determined set of parameters determined from a large-patient study.

Referring again to FIG. 5, it is apparent that for the above-described 200-patient study, errors in the PTT-based blood pressure measurement fall into two distinct categories, each represented by quadrants in the graph 120. The upper right-hand quadrant, labeled 'I' in the graph, consists of patients that have relatively stiff arteries for their age. For this demographic, PTT consistently underestimates the patient's blood pressure. The lower left-hand quadrant, labeled 'III' in the graph, consists of patients that have relatively elastic arteries for their age, and have blood pressures that PTT consistently overestimates.

Figures 6A, 6B:
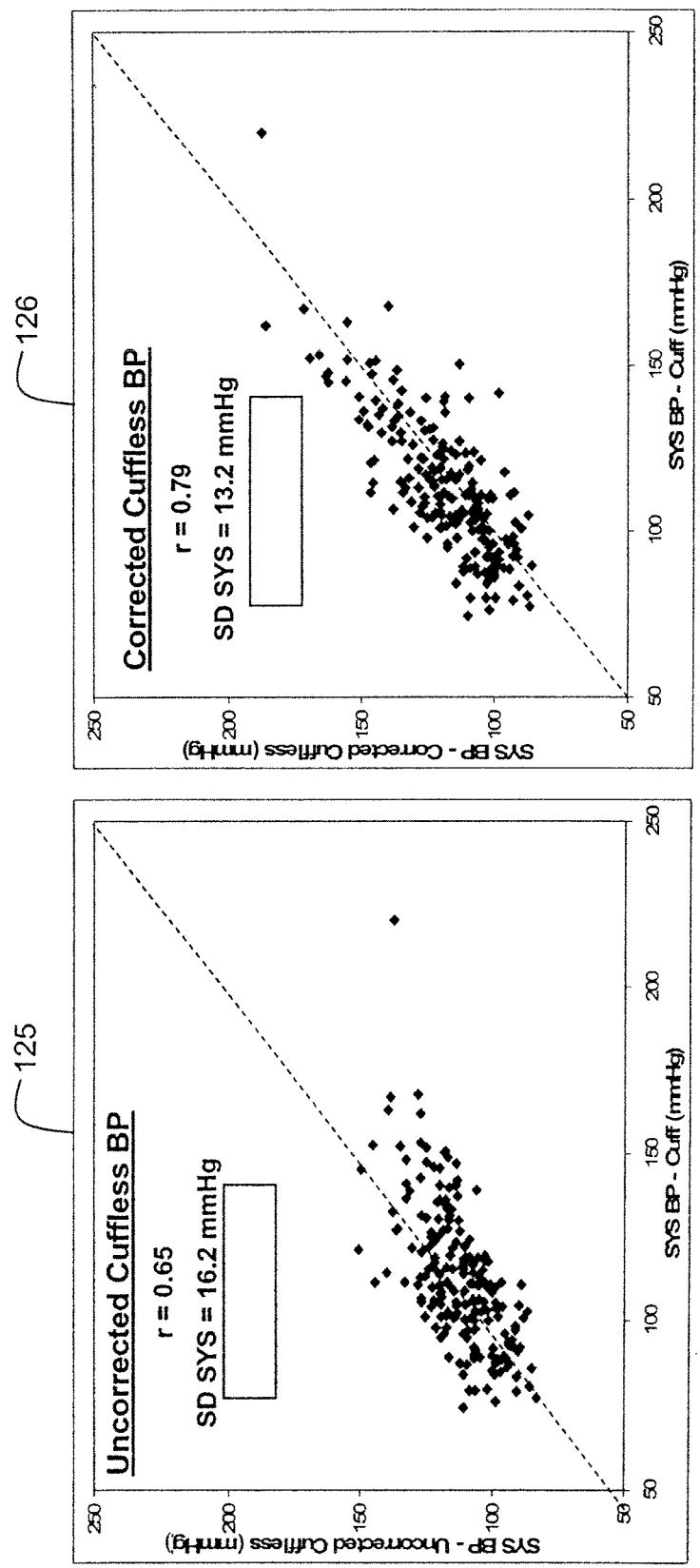
FIGS. 6A and 6B are graphs showing the correlation of systolic blood pressure measured with a cuff vs. systolic blood pressure measured according to the approach described herein determined, respectively, before and after the VI correction.

FIGS. 6A and 6B show graphs 125, 126 taken from the above-described 200-patient study, wherein systolic blood pressure, measured from PTT, is plotted against blood pressure simultaneously measured using a cuff-based aneroid sphygmomanometer. Uncorrected PTT-based blood pressure values are used in the first graph 125 (FIG. 6A), while corrected PTT-based blood pressure values are used in the second graph 126 (FIG. 6B). A relatively high correlation between the two blood pressure values in this type of study indicates that PTT can determine blood pressure with improved accuracy. As shown in FIG. 6A, without any VI correction, PTT-based systolic blood pressure correlates with cuff-based blood pressure with r=0.65 and a standard deviation (calculated from the difference of the two measurements) of 16.2 mmHg. PTT-based diastolic blood pressure (not shown in the graph) shows a standard deviation of 10.0 mmHg when compared to corresponding values measured with a cuff. These values, as shown with graph 126 in FIG. 6B, are significantly improved when the measurement is corrected for VI. Specifically, the VI correction improved the correlation (r=0.79) and standard deviations of both systolic (SD=±13.2 mmHg) and diastolic (SD=±8.2 mmHg) blood pressure. While the study used to generate these data is somewhat limited, it indicates that the VI correction improves the accuracy of PTT-determined blood pressure. Accurately measuring such high blood pressures is particularly important, as they are often used to identify patients in need of anti-hypertension therapy. High blood pressure is a known predictor of cardiovascular disease, such as stroke, coronary artery disease, heart failure, renal failure and cardiac arrest.

Figure 7:
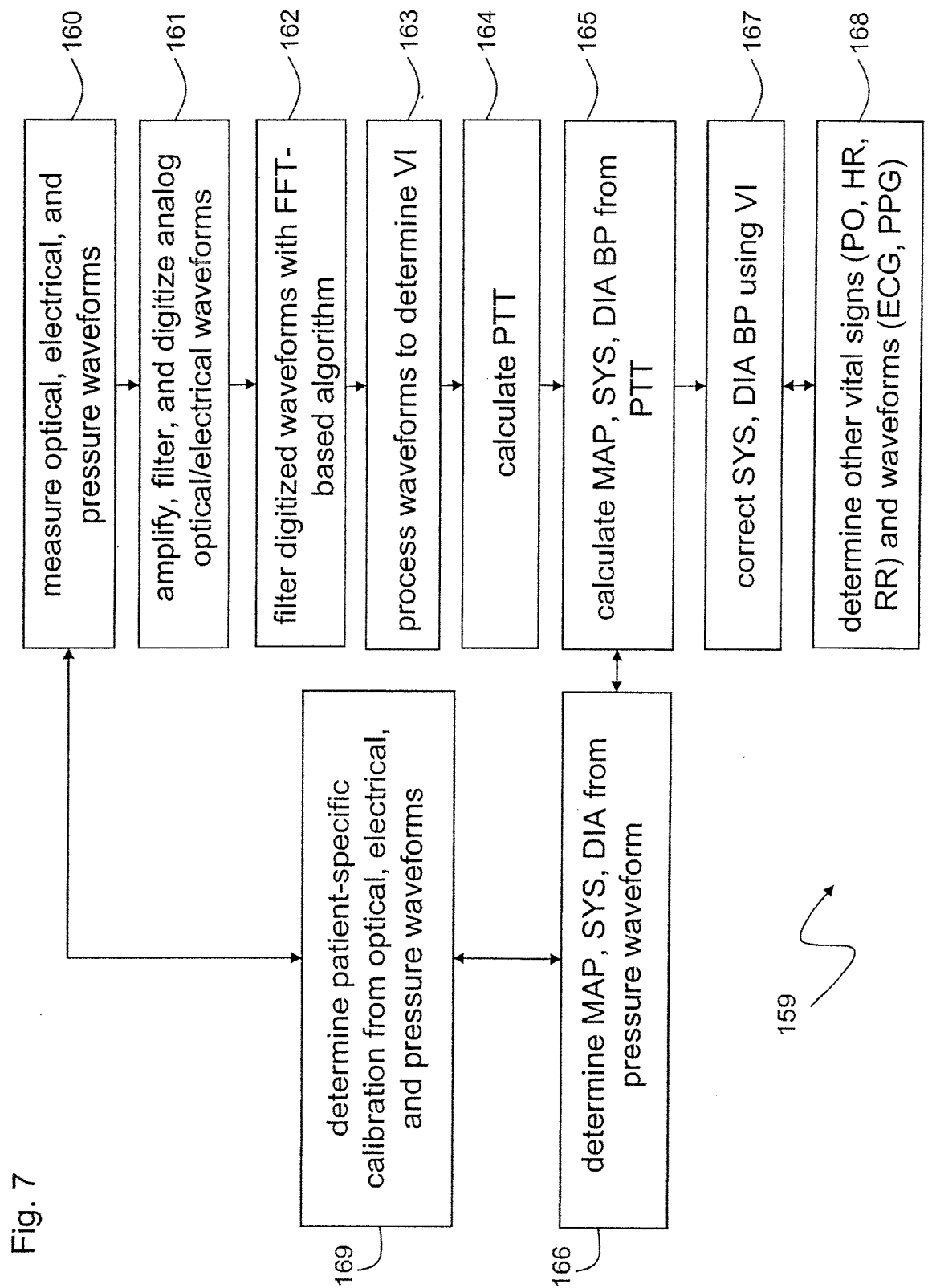
FIG. 7 is a flow chart showing an algorithm used to measure blood pressure by analyzing PTT and VI.

FIG. 7 shows a flowchart indicating an algorithm 159, based on the above-described study, which can be implemented with the device shown in FIGS. 1 and 2 during a blood pressure measurement. Prior to the measurement, a caregiver (or in another implementation, the patient) attaches the body sensor, armband and optical and electrical sensors to the patient. Once attached, the sensors simultaneously measure optical, electrical, and pressure waveforms (step 160), as described above. These analog signals pass through into the body sensor, where they are amplified (to increase signal strength) and filtered (to remove unwanted noise and correct for low-frequency modulation) with separate circuits, and finally digitized with an analog-to-digital converter (step 161). The optical, electrical, and pressure waveforms are processed to determine a patient-specific calibration (step 169), and the pressure waveform is processed to determine blood pressure values (step 166).

As shown in FIG. 4A, the digitized optical and electrical signals pass through FFT-based digital filters to remove unwanted noise (step 162). Once filtered, the resulting optical waveforms are processed by analyzing their second derivative as shown in FIGS. 4B, 4D, and 4F, and further filtered, as shown in FIGS. 4C and 4E, to determine peaks and troughs 'a' through 'e'. These parameters are then processed according to Equation 1 to determine VI (step 163). PTT is measured from the optical and electrical waveforms as shown in FIG. 8A (step 164), and then used to calculate mean arterial, systolic, and diastolic blood pressure (step 165) using the patient-specific calibration (step 169) and the initial blood pressure values determined from the pressure waveform (step 166). Once determined, the algorithm corrects systolic blood pressure using VI, biological age, and a set of predetermined coefficients according to Equation 2 (step 167). This correction accounts for patient-to-patient variation in arterial properties. Mean arterial pressure and diastolic pressure are determined in a similar method, or directly from systolic blood pressure using a predetermined mathematical relationship, e.g., a linear relationship characterized by a slope and y-intercept. The slope and y-intercept of this relationship are typically determined prior to the measurement using a large (typically n>100) clinical study.

Once blood pressure is determined, the optical and electrical waveforms can be further processed to determine other properties, such as heart rate, respiratory rate, and pulse oximetry (step 168). Pulse or heart rate, for example, is determined using techniques known in the art, e.g., determining the time spacing between pulses in the optical waveform, or QRS complexes in the electrical waveform, respectively. Respiratory rate modulates the time-dependent properties of the envelope of the optical and/or electrical waveforms, and thus can be determined, for example, by taking a spectral transform (e.g. a wavelet or Fourier transform) of these waveforms and then analyzing for low-frequency signals. The frequency of the envelope corresponds to the respiratory rate. Alternatively, respiratory rate can be calculated using an acoustic sensor, placed on the patient's chest, that measures breathing sounds. These two methodologies can be used in tandem and the signals used to corroborate respiratory rate. Pulse oximetry can be determined from the optical waveform using well-known algorithms, such as those described in U.S. Pat. No. 4,653,498 to New, Jr. et al., the contents of which are incorporated herein by reference. Pulse oximetry requires time-dependent signals generated from two or more, separate and modulated light sources (in the red spectral range and in the infrared).

The above-described method can be used in the composite technique, which features both pressure-dependent and pressure-free measurements. FIGS. 8A and 8B show schematic drawings of the composite technique's pressure-free (FIG.

8A) and pressure-dependent (FIG. 8B) measurements. Working in concert, these measurements accurately and continuously determine the patient's blood pressure for an extended time without requiring an external calibration device, e.g., a conventional blood pressure cuff. During a measurement, the patient wears a body sensor attached to a disposable armband and optical and electrical sensors. These sensors measure signals for both the pressure-dependent and pressure-free measurements. A microprocessor in the body sensor processes the optical and electrical waveforms to determine PTT, which is used in both measurements of the composite technique to determine blood pressure, as is described in more detail below.

The armband includes an air bladder which, when pressurized with a mechanical pump, applies a pressure 207 to an underlying artery 202, 202'. An electrical system featuring at least 3 electrodes coupled to an amplifier/filter circuit within the body sensor measures an electrical waveform 204, 204' from the patient. Three electrodes (two detecting positive and negative signals, and one serving as a ground) are typically required to detect the necessary signals to generate an electrical waveform with an adequate signal-to-noise ratio. At the same time, an optical system featuring a reflective optical sensor measures an optical waveform 205, 205' featuring a series of 'pulses', each characterized by an amplitude of $AMP_1$, $AMP_2$, from the patient's artery. Typical measurement sites are proximal to the brachial or radial arteries, or the smaller arteries near the base of the patient's thumb (e.g. on the palm side of the hand). A microprocessor and analog-to-digital converter within the body sensor detects and analyzes the electrical 204, 204' and optical 205, 205' waveforms to determine both $PTT_1$ (from the pressure-free measurement) and $PTT_2$ (from the pressure-dependent measurement). Typically the microprocessor determines both $PTT_1$ and $PTT_2$ by calculating the time difference between the peak of the QRS complex in the electrical waveform 204, 204' and the foot (i.e. onset) of the optical waveform 205, 205'.

The approach described herein is based on the realization that an applied pressure (indicated by arrow 207) during the pressure-dependent measurement affects blood flow (indicated by arrows 203, 203') in the underlying artery 202, 202'. Specifically, the applied pressure has no affect on either $PTT_2$ or $AMP_2$ when it is less than a diastolic pressure within the artery 202, 202'. When the applied pressure 207 reaches the diastolic pressure it begins to compress the artery, thus reducing blood flow and the effective internal pressure. This causes $PTT_2$ to systematically increase relative to $PTT_1$, and $AMP_2$ to systematically decrease relative to $AMP_1$. $PTT_2$ increases and $AMP_2$ decreases (typically in a linear manner) as the applied pressure 207 approaches the systolic blood pressure within the artery 202, 202'. When the applied pressure 207 reaches the systolic blood pressure, $AMP_2$ is completely eliminated and $PTT_2$ consequently becomes immeasurable.

Figure 9:
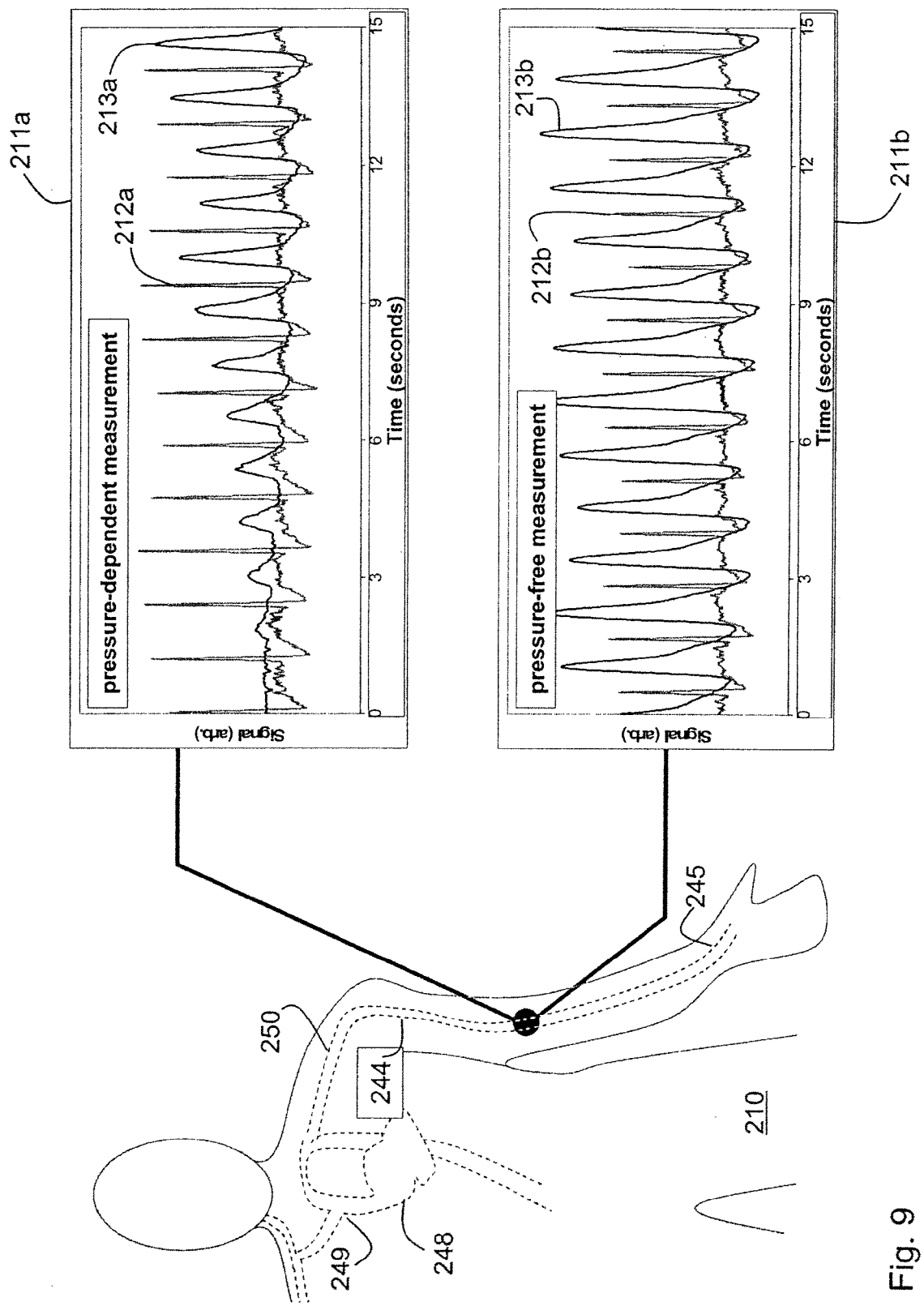
FIG. 9 shows a schematic drawing of a patient and optical and electrical waveforms measured during the pressure-dependent and pressure-free measurements of FIGS. 8A and 8B.

FIG. 9 illustrates the above-mentioned measurement in more detail. During a measurement the patient's heart 248 generates electrical impulses that pass through the body near the speed of light. These impulses accompany each heart beat, which then generates a pressure wave that propagates through the patient's vasculature at a significantly slower speed. Immediately after the heartbeat, the pressure wave leaves the heart 248 and aorta 249, passes through the subclavian artery 250, to the brachial artery 244, and from there through the radial and ulnar arteries 245 to smaller arteries in the patient's fingers. Three disposable electrodes located on the patient's chest measure unique electrical signals which pass to an amplifier/filter circuit within the body sensor. As described above, these electrodes attach to the patient's chest in a 1-vector 'Einthoven's triangle' configuration to measure unique electrical signals. Within the body sensor, the signals are processed using the amplifier/filter circuit to determine an analog electrical signal, which is digitized with an analog-to-digital converter to form the electrical waveform and then stored in memory. The optical sensor typically includes an optical module featuring an integrated photodetector, amplifier, and pair of light sources operating near 570 nm+/−10 nm. This wavelength is selected because it is particularly sensitive to volumetric absorbance changes in an underlying artery for a wide variety of skin types when deployed in a reflection-mode geometry. The optical sensor detects reflected radiation, which is further processed with a second amplifier/filter circuit within the body sensor. This results in the optical waveform, which, as described above, includes a series of pulses, each corresponding to an individual heartbeat.

During the composite technique, the same optical and electrical sensors are used during the pressure-dependent and pressure-free measurements to measure signals from the patient 210. Optical 213a, 213b and electrical 212a, 212b waveforms from these measurements are shown in the graphs 211a, 211b in the figure. In the top graph showing the pressure-dependent measurement pressure gradually decreases with time.

Each pulse in the optical waveforms 213a, 213b from both measurements corresponds to an individual heartbeat, and represents a volumetric absorbance change in an underlying artery caused by the propagating pressure pulse. Likewise, the electrical waveforms 212a, 212b from each measurement feature a series of sharp, 'QRS' complexes corresponding to each heartbeat. As described above, pressure has a strong impact on amplitudes of pulses in the optical waveform 213a during the pressure-dependent measurement, but has no impact on the amplitudes of QRS complexes in the corresponding electrical waveform 212a. These waveforms are processed as described below to determine blood pressure.

Figure 10:
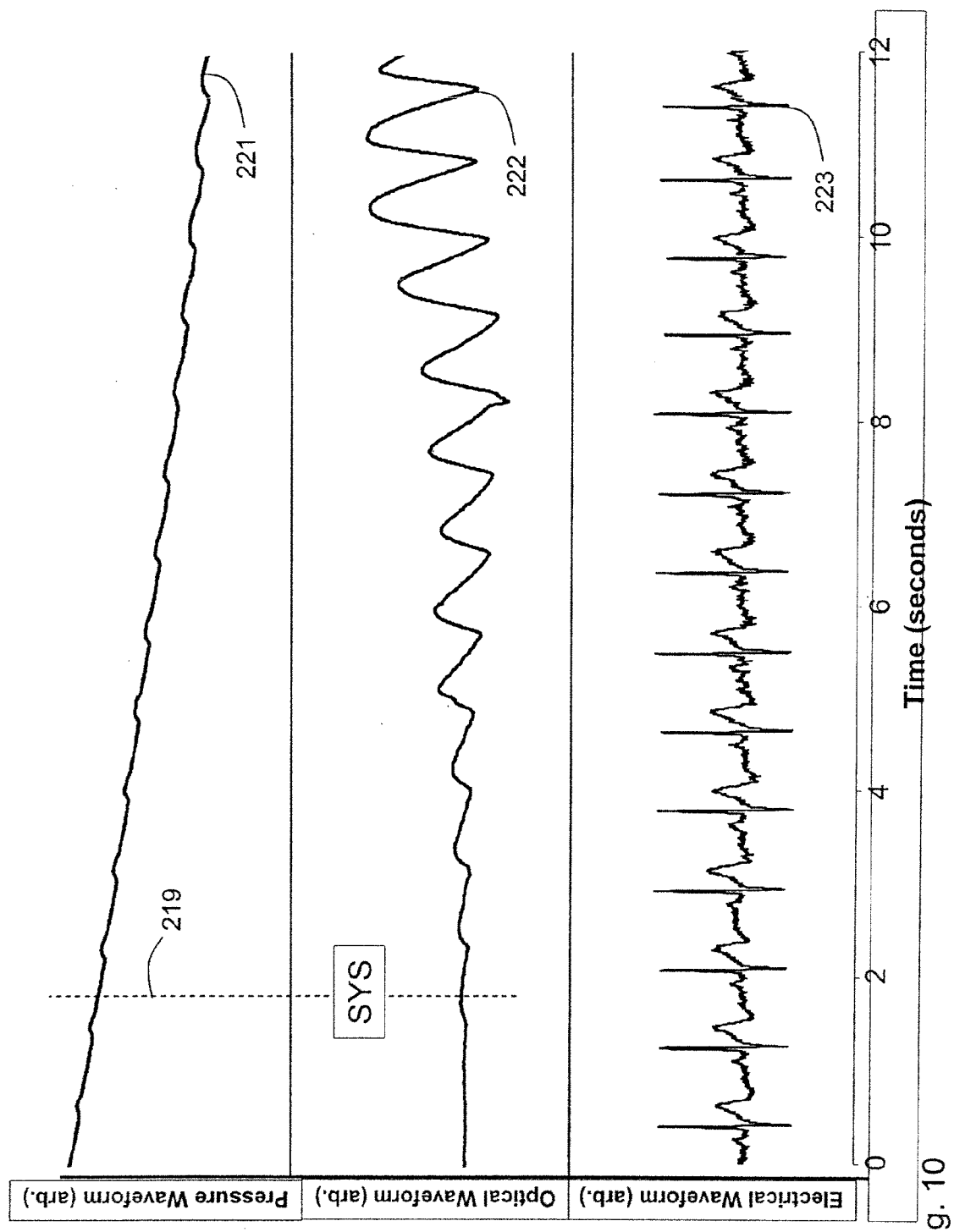
FIG. 10 shows graphs of time-dependent pressure, optical, and electrical waveforms measured with the body sensor and the optical, electrical, and pressure sensors.

FIG. 10 shows, in more detail, graphs of the time-dependent pressure 221, optical 222, and electrical 223 waveforms measured during the pressure-dependent measurement. FIGS. 11A and 11B show, respectively, how PTT and the optical pulse amplitude determined from the optical 222 and electrical 223 waveforms vary with applied pressure for a typical patient. Pulses in the optical waveform 222 have no amplitude when the applied pressure is greater than systolic pressure (indicated by the dashed line 219) in the underlying artery. The pulses begin to appear when the applied pressure is equivalent to systolic blood pressure. Their amplitude increases, and their PTT decreases, as applied pressure decreases. These trends continue until diastolic pressure is reached. At this point, the amplitude of the pulses and the associated PTT values are relatively constant. QRS complexes in electrical waveform 223 are unaffected by the applied pressure.

During an actual pressure-dependent measurement, the body sensor collects data like that shown in FIGS. 11A and 11B, for an individual patient. A conventional peak-detecting algorithm running on the microprocessor in the body sensor detects the onset of the optical pulse amplitude, shown in FIG. 11B, to make a direct measurement of systolic blood pressure. Alternatively, a 'fitting' algorithm can model the systematic decrease in pulse amplitude with applied pressure with a mathematical function (e.g. a linear function) to estimate systolic blood pressure.

Similarly, for a given patient, the microprocessor analyzes the variation between applied pressure and PTT, shown graphically in FIG. 11A, to estimate the relationship between blood pressure and PTT. As shown in Equation 3, below, this relationship is best described with a mathematical model that first estimates how the patient's 'effective' mean arterial blood pressure (MAP*(P)) varies with applied pressure ($P_{applied}$). The model assumes that pressure applied by the armband occludes the patient's brachial artery, and thus temporarily decreases blood flow. This, in turn, increases blood pressure directly underneath the armband, and reduces blood pressure in the downstream radial, ulnar, and finger arteries. The net effect is a temporary, pressure-dependent reduction in the patient's mean arterial blood pressure (MAP), indicated in equation 1 as ΔMAP(P), during the pressure-dependent measurement. An empirically determined factor (F) accounts for the ratio between the region of increased blood pressure (underneath the armband; approximately 10 cm) and the larger region of decreased blood pressure (the length of the arm downstream from the armband; approximately 50 cm). F is typically between 0.6 and 0.9, and is preprogrammed into the algorithm prior to measurement.

$$\Delta MAP(P) = F^{*}(P_{applied} - DIA)$$

$$MAP^{*}(P) = MAP - \Delta MAP(P) \quad\quad 3)$$

Using Equation 3, paired values of PTT and MAP*(P) are determined for each heartbeat as the applied pressure increases from the diastolic pressure to mean arterial pressure. This approach yields multiple data points during a single pressure-dependent measurement that can then be fit with a mathematical function (e.g. a linear function) relating PTT to mean arterial pressure. Typically these parameters are inversely related, i.e. PTT gets shorter and blood pressure increases. In typical embodiments, therefore, an inverse linear relationship determined during the pressure-dependent measurement is then used during subsequent pressure-free measurements to convert the measured PTT into blood pressure values.

In Equation 3, the values for diastolic blood pressure (DIA) and mean arterial pressure (MAP) are determined with an oscillometric blood pressure measurement during inflation. Systolic blood pressure (SYS) can either be determined indirectly during the oscillometric blood pressure measurement, or directly using the above-described method involving the pulse amplitude in the optical waveform. From these values, the SYS/MAP and DIA/MAP ratios can be determined. These ratios are typically constant for a given patient over a range of blood pressures. They can be used during the pressure-free measurements, along with the PTT-dependent mean arterial pressure, to determine systolic and diastolic blood pressures.

The oscillometric blood pressure measurement analyzes the pressure waveform (221 in FIG. 10) that is measured by the armband. Performing this measurement during inflation expedites the measurement and increases patient comfort. In contrast, most conventional cuff-based systems using the oscillometric technique analyze their pressure waveform during deflation, resulting in a measurement that is roughly 4 times longer than the composite technique's pressure-dependent measurement. Inflation-based measurements are possible because of the composite technique's relatively slow inflation speed (typically 5-10 mmHg/second) and the high sensitivity of the pressure sensor used within the body sensor. Moreover, measurements made during inflation can be immediately terminated once systolic blood pressure is calculated. In contrast, conventional cuff-based measurements made during deflation typically apply a pressure that far exceeds the patient's systolic blood pressure; pressure within the cuff then slowly bleeds down below the diastolic pressure to complete the measurement.

Other embodiments are also within the scope of the invention. For example, other properties of the optical waveform, such as the width, rise time, fall time, dichrotic notch, general shape, or any other feature that indicates arterial properties, can be used to estimate the stiffness of the patient's arteries and used along with PTT to improve the accuracy of the blood pressure measurement.

In other embodiments, software configurations other than those described above can be run on the bedside device to give it a PDA-like functionality. These include, for example, Micro C OS®, Linux®, Microsoft Windows®, embOS, VxWorks, SymbianOS, QNX, OSE, BSD and its variants, FreeDOS, FreeRTOX, LynxOS, or eCOS and other embedded operating systems. The device can also run a software configuration that allows it to receive and send voice calls, text messages, or video streams received through the Internet or from the nation-wide wireless network it connects to. A bar-code scanner can also be incorporated into the device to capture patient or medical professional identification information, or other such labeling. This information, for example, can be used to communicate with a patient in a hospital or at home. In other embodiments, the device can connect to an Internet-accessible website to download content, e.g., calibrations, software updates, text messages, and information describing medications, from an associated website. As described above, the device can connect to the website using both wired (e.g., USB port) or wireless (e.g., short or long-range wireless transceivers) means. In still other embodiments, 'alert' values corresponding to vital signs and the pager or cell phone number of a caregiver can be programmed into the device using its graphical user interface. If a patient's vital signs meet an alert criteria, software on the device can send a wireless 'page' to the caregiver, thereby alerting them to the patient's condition. For additional patient safety, a confirmation scheme can be implemented that alerts other individuals or systems until acknowledgment of the alert is received.

What is claimed:

1. A system for monitoring a patient's blood pressure parameter, the system comprising:
   an optical sensor configured to attach to the patient and generate a time-dependent optical waveform representing a flow of blood within the patient;
   an electrode system configured to attach to the patient and generate a time-dependent electrical waveform representing activity of the patient's heart;
   a calibration system configured to attach to a portion of the patient's body and apply a pressure; and
   a processing component programmed to: i) determine a first set of pulse transit times, wherein each transit time within the set is a measure of a separation in time of a first feature of the time-dependent electrical waveform and a second feature of the time-dependent optical waveform, the first set of pulse transit times measured while the calibration system applies the pressure to the portion of the patient's body; ii) analyze the first set of pulse transit times with a mathematical model that processes a pressure-induced change in transit time to determine a calibration representing properties of the patient's blood circulatory system; and iii) calculate the blood pressure parameter from a second pulse transit time and the calibration, the second pulse transit time measured while the calibration system does not apply pressure to the portion of the patient's body.

2. The system of claim 1, wherein the calibration represents the patient's vascular index.

3. The system of claim 2, wherein the calibration is linearly proportional to the vascular index.

4. The system of claim 2, wherein the processing component is programmed to analyze the time-dependent optical waveform by:
bandpass filtering the time-dependent optical waveform to generate a filtered waveform;
computing a derivative of the filtered waveform to generate a derivative waveform; and
computing the calibration from characteristics of a waveform derived from the derivative waveform.

5. The system of claim 4, wherein the processing component is further programmed to analyze the time-dependent optical waveform by filtering the derivative waveform to generate the derived waveform.

6. The system of claim 4, wherein the derivative that is used to generate the derivative waveform is the second derivative.

7. The system of claim 1, wherein the first feature of the time-dependent electrical waveform is a QRS complex and the second feature of the time-dependent optical waveform corresponds to an onset of a pressure pulse.

8. A method of monitoring a patient's blood pressure parameter, the method comprising:
detecting a time-dependent optical waveform from a flow of blood within the patient;
detecting a time-dependent electrical waveform representing activity of the patient's heart;
applying a pressure to a portion of the patient's body while detecting the optical waveform and the electrical waveform;
analyzing the time-dependent optical waveform and the time-dependent electrical waveform while pressure is applied to a portion of the patient's body to determine a set of pulse transit times featuring values that change with the amount of applied pressure, wherein each pulse transit time within the set is a measure of a separation in time of a first feature of the time-dependent electrical waveform and a second feature of the time-dependent optical waveform, the set of pulse transit times representing properties of the patient's blood circulatory system;
processing the pressure-dependent change in pulse transit times within the set of pulse transit times with a mathematical model to determine a calibration;
measuring a second pulse transit time for the patient while pressure is not applied to the portion of the patient's body; and
determining the blood pressure parameter from the second pulse transit time and the calibration.

9. The method of claim 8, wherein analyzing the time-dependent optical waveform involves:
bandpass filtering the time-dependent optical waveform to generate a filtered waveform;
computing a derivative of the filtered waveform to generate a derivative waveform; and
computing the calibration from characteristics of a waveform derived from the derivative waveform.

10. The method of claim 9, further comprising filtering the derivative waveform to generate the derived waveform.

11. The method of claim 9, wherein the derivative that is used to generate the derivative waveform is the second derivative.

12. The method of claim 9, wherein the first feature of the time-dependent electrical waveform is a QRS complex and the second feature of the time-dependent optical waveform corresponds to an onset of a pressure pulse.

13. A system for monitoring a patient's blood pressure parameter, the system comprising:
an optical sensor configured to attach to the patient and generate a time-dependent optical waveform representing a flow of blood within the patient;
an electrode system configured to attach to the patient and generate a time-dependent electrical waveform representing activity of the patient's heart;
a calibration system configured to attach to a portion of the patient and apply a pressure; and
a processing component programmed to: i) determine a set of pulse transit times while the calibration system applies pressure to the portion of the patient, with each pulse transit time within the set representing a measure of a separation in time of a first feature of the time-dependent electrical waveform and a second feature of the time-dependent optical waveform; ii) analyze the pressure-dependent change in values of pulse transit times within the set of pulse transit times with a mathematical model to determine a vascular index representing properties of the patient's blood circulatory system; and iii) use the vascular index and a pulse transit time measured when pressure is not applied by the calibration system to determine a value of a blood pressure parameter for the patient.

14. A method of monitoring a patient's blood pressure parameter, the method comprising:
generating a time-dependent optical waveform from a flow of blood within the patient;
detecting a time-dependent electrical waveform representing activity of the patient's heart;
applying a pressure to a portion of the patient's body;
analyzing the time-dependent optical waveform and the time-dependent electrical waveform while pressure is applied to a portion of the patient's body to determine a set of pulse transit times, with each transit time representing a measure of a separation in time of a first feature of the electrical waveform and a second feature of the optical waveform, and a pressure-dependent change in the values of transit times indicating a vascular index representing properties of the patient's blood circulatory system;
processing the pressure-dependent change in the values of transit times within the set of pulse transit times with a mathematical model to determine a calibration;
determining a pulse transit time for the patient when pressure is not applied to a portion of the patient's body; and
using the calibration and a measured pulse transit time for the patient to determine a value of the blood pressure parameter for the patient.

15. The system of claim 1, wherein the mathematical model is a linear model.

16. The system of claim 15, wherein the linear model relates a pressure-dependent change in estimated mean arterial pressure ($\Delta MAP(P_{applied})$) while pressure is applied by the calibration system to: i) the pressure applied ($P_{applied}$); applied); ii) a diastolic blood pressure measured by the calibration system (DIA); and iii) a mean arterial pressure measured by the calibration system (MAP).

17. The system of claim 16, wherein the linear model estimates the effective pressure-dependent mean arterial pressure in the portion of the patient's body (MAP*(P)) while pressure is applied.

18. The system of claim 17, wherein the linear model comprises the equations: $\Delta MAP(P) \sim (P_{applied} - DIA)$ and MAP*(P)=MAP−$\Delta MAP(P)$.

19. The system of claim 18, wherein the mathematical model estimates a mathematical relationship between pulse transit time and MAP*(P).

20. The system of claim 19, wherein the calibration comprises the mathematical relationship between pulse transit time and MAP*(P).

21. The system of claim 20, wherein a unique transit time is determined for each of the patient's heartbeats generated while pressure is applied by the calibration system.

22. A system for monitoring a patient's blood pressure parameter, comprising body-worn sensors for measuring optical and electrical waveforms, a pressure-applying calibration system, a first processing system for determining a transit time from the optical and electrical waveforms, a second processing system for calculating a calibration from a pressure-induced change in transit time caused by the calibration system, and a third processing system for calculating the blood pressure parameters from the calibration and a transit time.

23. A system for monitoring a patient's blood pressure parameter, the system comprising:

an optical sensor configured to attach to the patient and generate a time-dependent optical waveform representing a flow of blood within the patient;

an electrode system configured to attach to the patient and generate a time-dependent electrical waveform representing activity of the patient's heart; and a processing component programmed to: i) determine a first pulse transit time, which is a measure of a separation in time of a first feature of the time-dependent electrical waveform and a second feature of the time-dependent optical waveform; ii) analyze the optical waveform to determine its second mathematical derivative; iii) determine a set of fiducial points from the second mathematical derivative; iv) process the set of fiducial points with a mathematical model to estimate a vascular index representing properties of the patient's blood circulatory system; and v) determine an estimate of the blood pressure parameter from a measured second pulse transit time for the patient and the vascular index measured from the optical waveform used to calculate the second pulse transit time.

* * * * *